United States Patent [19]
Hawkins et al.

[11] Patent Number: 5,843,193
[45] Date of Patent: Dec. 1, 1998

[54] HAIR DYE COMPOSITIONS AND PROCESS

[75] Inventors: Geoffrey Robert Hawkins, Langhorne, Pa.; Terence Martin Dolak, Andover; Glenn Alan Gutkowski, Rahway, both of N.J.

[73] Assignee: Revlon Consumer Products Corporation, NY, N.Y.

[21] Appl. No.: 819,809

[22] Filed: Mar. 18, 1997

[51] Int. Cl.$^6$ .................................................... A61K 7/13
[52] U.S. Cl. ........................................ 8/408; 8/405; 8/406
[58] Field of Search ................................. 8/405, 406, 408, 8/409, 410, 411, 412, 414, 415, 416, 421, 423, 570, 573

[56] References Cited

U.S. PATENT DOCUMENTS

| | | | |
|---|---|---|---|
| Re. 33,786 | 1/1992 | Pohl et al. | 8/406 |
| 3,983,132 | 9/1976 | Strobel | 260/308 B |
| 4,096,242 | 6/1978 | Strobel | 424/59 |
| 4,129,521 | 12/1978 | Strobel | 252/403 |
| 4,322,212 | 3/1982 | Konrad | 8/407 |
| 4,587,346 | 5/1986 | Winter | 548/260 |
| 4,845,180 | 7/1989 | Henry | 528/73 |
| 4,921,966 | 5/1990 | Stegman | 548/260 |
| 4,973,701 | 11/1990 | Winter | 548/260 |
| 5,089,250 | 2/1992 | Forestier | 424/43 |
| 5,089,257 | 2/1992 | Schrader et al. | 424/70.13 |
| 5,254,333 | 10/1993 | Kajino et al. | 424/70.11 |
| 5,529,583 | 6/1996 | Lim et al. | 8/408 |
| 5,569,451 | 10/1996 | Richard | 424/59 |
| 5,645,609 | 7/1997 | Andrean et al. | 8/405 |
| 5,685,882 | 11/1997 | Samain et al. | 8/408 |

FOREIGN PATENT DOCUMENTS

| | | |
|---|---|---|
| 241707 | 10/1987 | European Pat. Off. . |
| 308825 | 3/1989 | European Pat. Off. . |
| 640335 | 3/1995 | European Pat. Off. . |
| 824909-A2 | 2/1998 | European Pat. Off. . |

OTHER PUBLICATIONS

Cibafast W technical Pamphlet 6002–74 Mar. 1994.
Textile World, vol. 142, No. 3, p. 64 Mar. 1992.

*Primary Examiner*—Robert H. Harrison
*Attorney, Agent, or Firm*—Julie Blackburn

[57] ABSTRACT

A composition for oxidative dyeing of hair comprising, by weight of the total composition:

- 0.0001–20% of at least one primary intermediate and at least one coupler for the formation of oxidation dyes,
- 0.01–10% of a 2-hydroxyphenyl benzotriazole compound which absorbs ultraviolet radiation in the wavelength range of 200 to 400 nanometers,
- 0.5–20% surfactant, and
- 10–65% water; a two component kit containing the hair dye composition and a developer, and a method for oxidative dyeing of hair with said kit.

17 Claims, No Drawings

HAIR DYE COMPOSITIONS AND PROCESS

TECHNICAL FIELD

The invention is in the field of methods and compositions for coloring hair.

BACKGROUND OF THE INVENTION

Oxidative dye systems are used for permanent coloration of hair. However, hair colored with oxidative dyes tends to fade upon exposure to sunlight, with red tones being particularly susceptible. Thus, there is a need for hair dye systems which exhibit improved resistance to fading upon exposure to ultraviolet light.

The object of the invention is to provide a hair color system which exibits improved resistance to color fading caused by ultraviolet light.

SUMMARY OF THE INVENTION

The invention is directed to a composition for oxidative dyeing of hair comprising, by weight of the total composition:

about 0.0001–20% (combined weight) of at least one primary intermediate and at least one coupler for the formation of oxidation dyes, about 0.01–10% of a 2-hydroxyphenyl benzotriazole compound which absorbs ultraviolet radiation in the wavelength range of 200 to 400 nanometers, about 0.5–20% surfactant, and about 10–65% water.

The invention is also directed to a two component kit for oxidative dyeing of hair comprising:

a first container containing a composition comprising, by weight of the total composition:

about 0.0001–20% (combined weight) of at least one primary intermediate and at least one coupler for the formation of oxidation dyes, about 0.01–10% of a 2-hydroxyphenyl benzotriazole compound which absorbs ultraviolet radiation in the wavelength range of 200 to 400 nanometers, about 0.5–20% surfactant, and about 10–65% water; and a second container containing a developer composition comprising, by weight of the total composition:

about 0.5–45% hydrogen peroxide, about 0.1–10% of a silicone conditioning agent, about 0.01–5% of an anionic polymer, and about 1–99% water.

The invention also comprises a method for oxidative dyeing of hair comprising the steps of:

a) applying to the hair a composition obtained by mixing Composition A and Composition B, wherein Composition A comprises, by weight of the total composition:

about 0.0001–20% (combined weight) of at least one primary intermediate and at least one coupler for the formation of oxidation dyes, about 0.01–10% of a 2-hydroxyphenyl benzotriazole compound which absorbs ultraviolet radiation in the wavelength range of 200 to 400 nanometers, about 0.5–20% surfactant, and about 10–65% water; and Composition B comprises, by weight of the total composition:

about 0.5–45% hydrogen peroxide, about 0.1–10% of a silicone conditioning agent, about 0.01–5% of an anionic polymer, and about 1–99% water, b) leaving said composition on the hair for 2 to 60 minutes, c) rinsing the hair with water.

DETAILED DESCRIPTION

All percentages mentioned herein are percentages by weight unless otherwise indicated. The compositions of the invention have a pH ranging from 7 to 11, and Composition A preferably contains 65% or less of water.

PRIMARY INTERMEDIATES AND COUPLERS

The compositions contain 0.0001–20%, preferably 0.001–15%, more preferably 0.01–10% (combined weight) of at least one primary intermediate and at least one coupler. Preferably, the range of primary intermediate will be about 0.0001–5% by weight and the range of coupler will be about 0.0001–5% by weight. Primary intermediates and couplers are well known hair coloring ingredients, and include ortho or para substituted aminophenols or phenylenediamines, such as para-phenylenediamines of the formula:

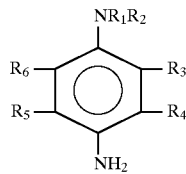

wherein $R_1$ and $R_2$ are each independently hydrogen, $C_{1-6}$alkyl, or $C_{1-6}$alkyl substituted with one or more hydroxy, methoxy, methylsulphonylamino, aminocarbonyl, furfuryl, unsubstituted phenyl, or amino substituted phenyl groups; $R_3$ and $R_6$ are each independently hydrogen, $C_{1-6}$ alkyl, $C_{1-6}$alkoxy, halogen, or $C_{1-6}$alkyl substituted with one or more hydroxyl groups; and $R_4$ and $R_5$ are each independently hydrogen, $C_{1-6}$ lower alkoxy, $C_{1-6}$ lower alkyl, or halogen. Examples of suitable primary intermediates are para-aminophenol, para-diphenol, ortho-aminophenols, ortho-phenylenediamines, ortho-diphenols, and heterocyclic compounds. Examples of suitable primary intermediates include para-phenylenediamine, 2-methyl-1,4-diaminobenzene, 2,6-dimethyl-1,4-diaminobenzene, 2,5-dimethyl-1,4-diaminobenzene, 2,3-dimethyl-1,4-diaminobenzene, 2-chloro-1,4-diaminobenzene, 2-methoxy-1,4-diaminobenzene, 1-phenylamino-4-aminobenzene, 1-dimethylamino-4-aminobenzene, 1-diethylamino-4-aminobenzene, 1-bis(beta-hydroxyethyl)amino-4-aminobenzene, 1-methoxyethylamino-4-aminobenzene, 2-hydroxymethyl-1,4-diaminobenzene, 2-hydroxyethyl-1,4-diaminobenzene, 2-isopropyl-1,4-diaminobenzene, 1-hydroxypropyl-4-aminobenzene, 2,6-dimethyl-3-methoxy-1,4-diaminobenzene, 1-amino-4-hydroxybenzene, and derivatives thereof.

Preferred primary intermediates are p-phenylenediamine, p-aminophenol, o-aminophenol, N,N-bis(2-hydroxyethyl)-p-phenylenediamine, 2,5-diaminotoluene, their salts and mixtures thereof.

Suitable couplers include, for example, those having the general formula:

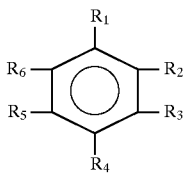

wherein $R_1$ is unsubstituted hydroxy or amino, or hydroxy or amino substituted with one or more $C_{1-6}$ hydroxyalkyl groups, $R_3$ and $R_5$ are each independently hydrogen, hydroxy, amino, or amino substituted with $C_{1-6}$ alkyl, $C_{1-6}$ alkoxy, or $C_{1-6}$ hydroxyalkyl group; and $R_2$, $R_4$, and $R_6$ are each independently hydrogen, $C_{1-6}$ alkoxy, $C_{1-6}$ alkoxy, $C_{1-6}$ hydroxyalkyl, or $C_{1-6}$ alkyl, or $R_3$ and $R_4$ together may form a methylenedioxy group. Examples of such compounds include meta-derivatives such as phenols, meta-diphenols, meta-aminophenols, meta-phenylenediamines, and the like, which may be unsubstituted, or substituted on the amino group or benzene ring with alkyl, hydroxyalkyl, alkylamino groups, and the like. Suitable couplers include 3,4-methylenedioxyphenol, 3,4-methylenedioxy-1-[(beta-hydroxyethyl)amino]benzene, 1-methoxy-2-amino-4-[(beta-hydroxyethyl)amino]benzene, 1-hydroxy-3-(dimethylamino)benzene, 6-methyl-1-hydroxy-3[(beta-hydroxyethyl)amino]benzene, 2,4-dichloro-1-hydroxy-3-aminobenzene, 1-hydroxy-3-(diethylamino)benzene, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethyloxy-1,3-diaminobenzene, 6-methoxy-5-ethyl-1,3-diaminobenzene, 6-ethyloxy-1,3-diaminobenzene, 1-bis(beta-hydroxyethyl)amino-3-aminobenzene, 2-methyl-1,3-diaminobenzene, 6-methoxy-1-amino-[(beta-hydroxyethyl)amino]-benzene, 6-(beta-aminoethyloxy)-1,3-diaminobenzene, 6-(beta-hydroxyethyloxy)-1-amino-3-(methylamino)benzene, 6-carboxymethyloxy-1,3-diaminobenzene, 6-ethyloxy-1-bis(beta-hydroxyethyl)amino-3-aminobenzene, 6-hydroxyethyl-1,3-diaminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-amino-benzene, 1-hydroxy-3-(carbamoylmethylamino) benzene, 6-hydroxybenzomorpholine, 4-methyl-6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene, 1,5-dihydroxynaphthalene, and mixtures thereof.

Preferred couplers include resorcinol, 1-naphthol, 5-amino-o-cresol, 2-methylresorcinol, m-aminophenol, m-phenylenediamine, 1-ohenyl-3-methyl-pyrazol-5-one, their salts, or mixtures thereof.

THE 2-HYDROXYPHENYL BENZOTRIAZOLE COMPOUND

The compositions of the invention contain 0.01–10%, preferably 0.01–8%, more preferably 0.01–5% of a 2-hydroxyphenyl benzotriazole compound which is capable of absorbing ultraviolet radiation in the wavelength range of 200 to 400 nanometers, preferably about 250 to 390 nanometers. It should be noted that many of the primary intermediates and couplers found in hair dyes are capable of absorbing ultraviolet (UV) radiation in this wavelength range, and it is believed that this is one reason why hair colors will fade upon exposure to UV light. Without being bounnd by this explanation, it is believed that the benzotriazole compounds used in the compositions of the invention at least partially permeate the hair shaft, in addition to complexing with the outer surface of the hair fiber. It is believed that they are capable of acting as primary absorbers of UV radiation, thereby preventing, or at least reducing, the tendency of the hair dye molecules themselves to absorb UV radiation and consequently be degraded.

Suitable 2-hydroxyphenyl benzotriazole compounds for use in the compositions of the invention can be distinguished from hair dye molecules because, preferably, they do not contain amino group substituents. The 2-hydroxyphenyl benzotriazoles suitable for use in the compositions of the invention correspond to one of the the general formulas (a), (b) and (c), set forth below:

Formula (a) compounds have the general formula:

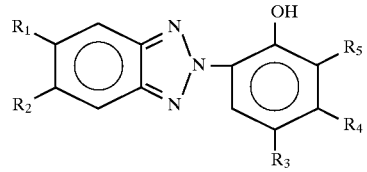

wherein $R_1$, $R_2$, $R_3$, $R_4$, and $R_5$ are each independently H, hydroxyl, carboxyl, halogen, or $C_{1-40}$ straight or branched chain alkyl, $C_{1-40}$ straight or branched chain alkoxy, $C_{2-20}$ alkoxycarbonyl, $C_{1-40}$ alkyl substituted phenyl, $C_{5-6}$ cycloalkyl, $SO_3H$, $SO_3Na$, or

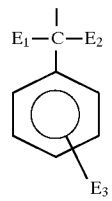

wherein $E_1$ and $E_2$ are each independently H or $C_{1-4}$ alkyl, and $E_3$ is H, halogen, or $C_{1-4}$ alkyl; $R_3$ is H, halogen, OH, $C_{1-40}$ straight or branched chain alkyl, $SO_3Na$, $C_{5-6}$ cycloalkyl, phenyl, $C_{1-10}$ alkyl substituted phenyl, or

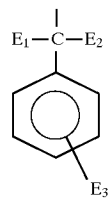

wherein $E_1$ and $E_2$ are each independently H, or $C_{1-4}$ alkyl, and $E_3$ is H, halogen, or $C_{1-4}$ straight or branched chain alkyl.

Examples of such compounds are disclosed in U.S. Pat. Nos. 5,240,975; 4,904,712; 4,921,966; 5,097,041; 5,095,062; 4,973,701; 4,587,346; and 4,675,352.

Formula (b) compounds have the general formula:

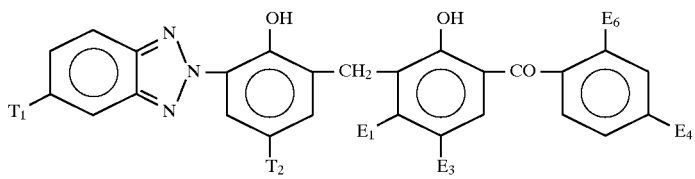

wherein
$T_1$ is hydrogen, halogen, $C_{1-4}$ alkyl, $SO_3H$, or $SO_3Na$,
$T_2$ is $C_{1-12}$ alkyl, $SO_3H$ or $SO_3Na$
$E_1$ is hydrogen, halogen, or —$OE_2$
$E_2$ is hydrogen, or $C_{1-18}$ alkyl,
$E_3$ is hydrogen, $C_{1-4}$ alkyl, halogen, $SO_3H$, or $SO_3Na$,
$E_4$ is hydrogen, halogen, or $OE_5$
$E_5$ is hydrogen or $C_{1-18}$ alkyl, and
$E_6$ is hydrogen, hydroxyl, or carboxyl.

Examples of such compounds are disclosed in U.S. Pat. No. 5,387,691, which is hereby incorporated by reference.

Also suitable are 2-hydroxyphenyl benzotriazole esters having the following general formula (c):

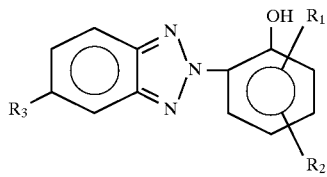

wherein $R_1$, $R_2$, and $R_3$ are each independently hydrogen, halogen, or an ester-containing radical with the proviso that there is at least one ester-containing radical. Examples of such 2-hydroxyphenyl benzotriazole esters are disclosed in U.S. Pat. No. 4,996,326, which is hereby incorporated by reference.

Also suitable as the 2-hydroxyphenyl benzotriazole compound for use in the compositions of the invention are fluorinated benzotriazole compounds having the general formula (d):

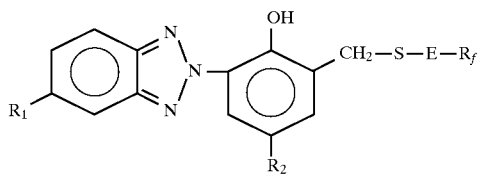

wherein
$R_1$ is hydrogen, halogen, $C_{1-4}$ alkyl, or $C_{1-4}$ alkoxy,
$R_2$ is $C_{1-8}$ alkyl, cycloalkyl of 5 to 12 carbon atoms, or phenylalkyl of 7 to 15 carbon atoms,
E is a branched or straight chain alkylene of 1 to 10 carbon atoms or said alkylene interrupted by one to three groups selected from the group consisting of —O—, —S—, —$SO_2$—, —COO—, —OOC—, and $R_f$ is a straight or branched chain perfluoroalkyl of 1 to 12 carbon atoms, perfluoroalkyl of 2 to 6 carbon atoms substituted by one or more perfluoroalkoxy groups of 2 to 6 carbon atoms, or an oligo(hexafluoropropene oxide) terminal group. Examples of such compounds are set forth in U.S. Pat. No. 5,312,852, which is hereby incorporated by reference.

Preferred are the Formula (a) compounds wherein $R_1$ and $R_2$ are both H. A more preferred subset are those compounds wherein $R_1$ and $R_2$ are both H, and $R_3$ is $SO_3Na$ or $SO_3H$. A preferred subset of the latter group are those compounds wherein $R_1$, $R_2$ and $R_4$ are H, $R_3$ is $SO_3Na$ or $SO_3H$, and $R_5$ is a $C_{1-10}$ straight or branched chain alkyl. Most preferred is a compound wherein $R_1$, $R_2$, and $R_4$ are H, $R_3$ is $SO_3Na$, and $R_5$ is a $C_{1-10}$ branched chain alkyl. Once example is the compound having the CTFA name sodium isobutyl benzotriazole sulfonate. This material may be purchased from Ciba-Geigy under the tradename Cibafast W Liquid, which is an anionic material.

THE SURFACTANT

The compositions of the invention comprise 0.5–20%, preferably 0.5–15%, more preferably 0.5–10%, of a surfactant. Suitable surfactants may be anionic, nonionic, amphoteric, or zwitterionic.

Anionic Surfactants

Anionic surfactants include alkyl and alkyl ether sulfates generally having the formula $ROSO_3M$ and $RO(C_2H_4O)_xSO_3M$ wherein R is alkyl or alkenyl of from about 10 to 20 carbon atoms, x is 1 to about 10 and M is a water soluble cation such as ammonium, sodium, potassium, or triethanolamine cation.

Another type of anionic surfactant which may be used in the compositions of the invention are water soluble salts of organic, sulfuric acid reaction products of the general formula:

$$R_1-SO_3-M$$

wherein $R_1$ is chosen from the group consisting of a straight or branched chain, saturated aliphatic hydrocarbon radical having from about 8 to about 24 carbon atoms, preferably 12 to about 18 carbon atoms; and M is a cation. Examples of such anionic surfactants are salts of organic sulfuric acid reaction products of hydrocarbons such as n-paraffins having 8 to 24 carbon atoms, and a sulfonating agent, such as sulfur trioxide.

Also suitable as anionic surfactants are reaction products of fatty acids esterified with isethionic acid and neutralized with sodium hydroxide. The fatty acids may be derived from coconut oil, for example.

In addition, succinates and succinimates are suitable anionic surfactants. This class includes compounds such as disodium N-octadecylsulfosuccinate; tetrasodium N-(1,2-dicarboxyethyl)-N-octadecylsulfosuccinate; and esters of sodium sulfosuccinic acid e.g. the dihexyl ester of sodium sulfosuccinic acid, the dioctyl ester of sodium sulfosuccinic acid, and the like.

Other suitable anionic surfactants include olefin sulfonates having about 12 to 24 carbon atoms. The term "olefin sulfonate" means a compound that can be produced by sulfonation of an alpha olefin by means of uncomplexed sulfur trioxide, followed by neutralization of the acid reaction mixture in conditions such that any sultones which have been formed in the reaction are hydrolyzed to give the corresponding hydroxy-alkanesulfonates. The alpha-olefin from which the olefin sulfonate is derived is a mono-olefin having about 12 to 24 carbon atoms, preferably about 14 to 16 carbon atoms.

Other classes of suitable anionic organic surfactants are the beta-alkoxy alkane sulfonates or water soluble soaps thereof such as the salts of $C_{10-20}$ fatty acids, for example coconut and tallow based soaps. Preferred salts are ammonium, potassium, and sodium salts.

Still another class of anionic surfactants include N-acyl amino acid surfactants and salts thereof (alkali, alkaline earth, and ammonium salts) having the formula:

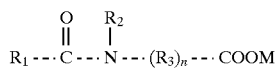

wherein $R_1$ is a $C_{8-24}$ alkyl or alkenyl radical, preferably $C_{10-18}$; $R_2$ is H, $C_{1-4}$ alkyl, phenyl, or $-CH_2COOM$; $R_3$ is $CX_2-$ or $C_{1-2}$ alkoxy, wherein each X independently is H or a $C_{1-6}$ alkyl or alkylester, n is from 1 to 4, and M is H or a salt forming cation as described above. Examples of such surfactants are the N-acyl sarcosinates, including lauroyl sarcosinate, myristoyl sarcosinate, cocoyl sarcosinate, and oleoyl sarcosinate, preferably in sodium or potassium forms.

Nonionic Surfactants

The composition can contain one or more nonionic surfactants in lieu of, or in addition to, the anionic surfactant. Nonionic surfactants are generally compounds produced by the condensation of alkylene oxide groups with a hydrophobic compound. Classes of nonionic surfactants are:

(a) Long chain dialkyl sulfoxides containing one short chain alkyl or hydroxy alkyl radical of from about 1 to 3 carbon atoms and one long hydrophobic chain which may be an alkyl, alkenyl, hydroxyalkyl, or ketoalkyl radical containing from about 8 to 20 carbon atoms, from 0 to 10 ethylene oxide moieties, and 0 or 1 glyceryl moiety.

(b) Polysorbates, such as sucrose esters of fatty acids. Examples of such materials include sucrose cocoate, sucrose behenate, and so on.

(c) Polyethylene oxide condensates of alkyl phenols, for example the condensation products of alkyl phenols having an alkyl group of 6 to 20 carbon atoms with ethylene oxide being present in amounts of about 10 to 60 moles of ethylene oxide per mole of alkyl phenol.

(d) Condensation products of ethylene oxide with the reaction product of propylene oxide and ethylene diamine.

(e) Condensation products of aliphatic alcohols having 8 to 18 carbon atoms with ethylene oxide, for example a coconut alcohol/ethylene oxide condensate having 10 to 30 moles of ethylene oxide per mole of coconut alcohol, the coconut alcohol fraction having 10 to 14 carbon atoms.

(f) Long chain tertiary amine oxides such as those corresponding to the general formula:

$$R_1R_2R_3NO$$

wherein $R_1$ contains an alkyl, alkenyl or monohydroxyalkyl radical ranging from about 8 to 18 carbon atoms in length, from 0 to about 10 ethylene oxide moieties, and from 0 to about 1 glyceryl moiety and $R_2$ and $R_3$ are each alkyl or monohydroxyalkyl groups containing from about 1 to about 3 carbon atoms.

(g) Long chain tertiary phosphine oxides corresponding to the general formula:

$$RR_1R_2PO$$

wherein R contains an alkyl, alkenyl, or monohydroxyalkyl radical having 8 to 18 carbon atoms, from 0–10 ethylene oxide moieties and 0 or 1 glyceryl moiety, and $R_2$ and $R_3$ are each alkyl or monohydroxyalkyl group containing from about 1 to 3 carbon atoms.

(h) Alkyl polysaccharides having a hydrophobic group of 6 to 30, preferably 10, carbon atoms and a polysaccharide group such as glucose, galactose, etc. Suitable alkyl polysaccharides are octyl, nonydecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses, and so on.

(i) Polyethylene glycol (PEG) glyceryl fatty esters, having the formula $$RC(O)OCH_2CH(OH)CH_2(OCH_2CH_2)_nOH$$

wherein n is 5–200 and RC(O)— is a hydrocarbylcarbonyl group wherein R is preferably an aliphatic radical having 7 to 19 carbon atoms.

(j) Other nonionic surfactants that may be used include $C_{10-18}$ alkyl($C_{1-6}$)polyhydroxy fatty acid amides such as $C_{12-18}$ methylglucamides, N-alkoxy polyhydroxy fatty acid amides, N-propyl through N-hexyl $C_{12-18}$ glucamides and so on.

Amphoteric Surfactants

Amphoteric surfactants that can be used in the compositions of the invention are generally described as derivatives of aliphatic secondary or tertiary amines wherein one aliphatic radical is a straight or branched chain alkyl of 8 to 18 carbon atoms and the other aliphatic radical contains an anionic group such as carboxy, sulfonate, sulfate, phosphate, or phosphonate.

Suitable amphoteric surfactants may be imidazolinium compounds having the general formula:

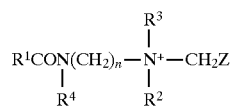

wherein $R^1$ is $C_{8-22}$ alkyl or alkenyl, preferably $C_{12-16}$; $R^2$ is hydrogen or $CH_2CO_2M$, $R^3$ is $CH_2CH_2OH$ or $CH_2CH_2OCH_2CHCOOM$; $R^4$ is hydrogen, $CH_2CH_2OH$, or $CH_2CH_2OCH_2CH_2COOM$, Z is $CO_2M$ or $CH_2CO_2M$, n is 2 or 3, preferably 2, M is hydrogen or a cation such as an alkali metal, alkaline earth metal, ammonium, or alkanol ammonium. cation. Examples of such materials are marketed under the tradename MIRANOL, by Miranol, Inc.

Also suitable amphoteric surfactants are monocarboxylates or dicarboxylates such as cocamphocarboxypropionate, cocoamphocarboxypropionic acid, cocamphocarboxyglycinate, and cocoamphoacetate.

Other types of amphoteric surfactants includ aminoalkanoates of the formula

or iminodialkanoates of the formula:

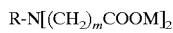

and mixtures thereof; wherein n and m are 1 to 4, R is $C_{8-22}$ alkyl or alkenyl, and M is hydrogen, alkali metal, alkaline earth metal, ammonium or alkanolammonium. Examples of such amphoteric surfactants include n-alkylaminopropionates and n-alkyliminodipropionates, which are sold under the trade name MIRATAINE by Miranol, Inc. or DERIPHAT by Henkel, for example N-lauryl-beta-amino propionic acid, N-lauryl-beta-imino-dipropionic acid, or mixtures thereof.

Zwitterionic surfactants are also suitable for use in the compositions of the invention. The general formula for such surfactants is:

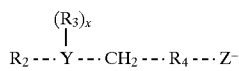

wherein $R_2$ contains an alkyl, alkenyl or hydroxy alkyl radical of from about 8 to about 18 carbon atoms, from 0 to about 10 ethylene oxide moieties and 0 or 1 glyceryl moiety; Y is selected from the group consisting of nitrogen, phosphorus, and sulfur atoms; $R_3$ is an alkyl or monohydroxyalkyl group containing about 1 to 3 carbon atoms; X is 1 when Y is a sulfur atom, and 2 when Y is a nitrogen or phosphorus atom; $R_4$ is an alkylene or hydroxyalkylene of from about 1 to about 4 carbon atoms, and Z is a radical selected from the group consisting of carboxylate, sulfonate, sulfate, phosphonate, and phosphate groups.

Zwitterionics include betaines, for example higher alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxylethyl betaine, and mixtures thereof. Also suitable are sulfo- and amido- betaines such as coco dimethyl sulfopropyl betaine, stearyl dimethyl sulfopropyl betaine, and the like.

In addition, the compositions of the invention may contain a number of other ingredients. Preferably the compositions of the invention comprise 0.01–15%, preferably 0.05–10%, preferably 0.10–8% of a cationic conditioning agent which is a cationic polymer, a quaternary ammonium salt or the salt of a fatty amine. Quaternary ammonium salts have the formula:

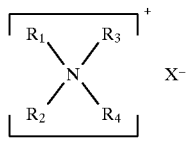

wherein $R_1$ is hydrogen, an aliphatic group of 1 to 22 carbon atoms, or aromatic, aryl, or alkaryl group having 12 to 22 carbon atoms; $R_2$ is an aliphatic group having 1–22 carbon atoms; $R_3$ and $R_4$ are each alkyl groups of from 1 to 3 carbon atoms, and X is an anion selected from halogen, acetate, phosphate, nitrate and methyl sulfate radicals. The aliphatic groups may contain, in addition to carbon and hydrogen atoms, ether linkages as well as amido groups. Suitable quaternary ammonium compounds may be mono-long chain alkyl, di-long chain alkyl, tri-long chain alkyl, and the like. Examples of such quaternary ammonium salts include behenalkonium chloride, behentrimonium chloride, behentrimonium methosulfate, benzalkonium chloride, benzethonium chloride, benzyl triethyl ammonium chloride, cetalkonium chloride, cetrimonium chloride, cetrimonium bromide, cetrimonium methosulfate, cetrimonium tosylate, cetylpyridinium chloride, dibehenyl/diarachidyl dimonium chloride, dibehenyldimonium chloride, dibehenyldimonium methosulfate, dicapryl/dicaprylyl dimonium chloride, dicetyldimonium chloride, and mixtures thereof.

Other quaternary ammonium salts useful as the cationic conditioning agent are compounds of the general formula:

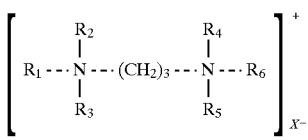

wherein $R_1$ is an aliphatic group having 16 to 22 carbon atoms, $R_2$, $R_3$, $R_4$, $R_5$, and $R_6$ are the same or different and are selected from H and alkyls having 1 to 4 carbon atoms and X is an anion as above defined.

Also, quaternary imidazolinium salts having the following general formula are also suitable:

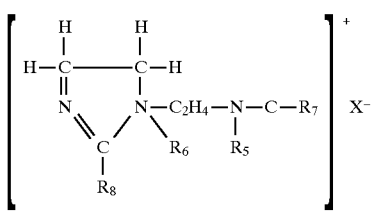

wherein $R_5$ is hydrogen or a $C_{1-4}$ alkyl; $R_6$ is a $C_{1-4}$ alkyl; $R_7$ is a $C_{8-22}$ alkyl; and $R_8$ is hydrogen, or a $C_{1-22}$ alkyl; and X is an anion as defined above.

Also suitable as the cationic hair conditioning agent are salts of fatty primary, secondary, or tertiary amines, wherein the substituted groups have 12 to 22 carbon atoms. Examples of such amines include dimethyl stearamine, dimethyl soyamine, stearylamine, myristylamine, tridecylamine, ethyl stearamine, and so on.

Also suitable as the cationic conditioning agent are cationic polymers such as:

(a) Quaternary derivatives of cellulose ethers such as polymers sold under the tradename JR-125, JR-400, JR-30M. Preferred is Polyquaternium 10, which is a polymeric quaternary ammonium salt of hydroxyethyl cellulose reacted with a trimethyl ammonium substituted epoxide.

(b) Copolymers of vinylpyrrolidone having monomer units of the formula:

$$\left[ \begin{array}{c} \text{N} \diagup \diagdown \text{O} \\ | \\ \text{—CH—CH}_2\text{—} \end{array} \right]_n \left[ \begin{array}{c} R^1 \\ | \\ \text{—CH}_2\text{—C—} \\ | \\ (C=O)_y \\ | \\ R_2 \\ | \\ R_3 \\ | \\ N^+(R_4)_2R_5X^- \end{array} \right]_m$$

wherein $R^1$ is hydrogen or methyl, preferably methyl;
y is 0 or 1, preferably 1
$R_1$ is O or NH, preferably NH;
$R^3$ is $C_xH_{2x}$ where x is 2 to 18, or —CH$_2$—CHOH—CH$_2$—, preferably $C_xH_{2x}$ where x is 2;
$R^4$ is methyl, ethyl, phenyl, or $C_{1-4}$ substituted phenyl, preferably methyl; and
$R^5$ is methyl or ethyl, preferably methyl.

Preferred are compounds of the above formula wherein y is 1, $R^2$ is NH, $R^3$ is CH$_2$CH$_2$, $R^4$ is methyl, and $R^5$ is methyl. Such compounds are known by the CTFA designation Polyquaternium 28.

(c) Homopolymer of dimethyldiallylammonium chloride, or copolymer of dimethyldiallylammonium chloride and acrylamide. Such compounds are sold under the tradename MERQUAT™ by Merck.

(d) Homopolymers or copolymers derived from acrylic or methacrylic acid wherein the monomer units are selected from the group consisting of acrylamide, methylacrylamide, diacetone-acrylamide, acrylamide or methacrylamide substituted on the nitrogen by lower alkyl, alkyl esters of acrylic acid and methacrylic acid, vinylpyrrolidone, and vinyl esters.

Examples of cationic polymers that can be used in the compositions of the invention are the cationic polymers disclosed in U.S. Pat. Nos. 5,240,450 and 5,573,709, which are hereby incorporated by reference.

The preferred compositions of the invention contain 0.01–10%, preferably 0.05–5%, more preferably 0.1–3%, of a fatty oil. The term "fatty oil" means an oil which is a liquid or semi-solid at room temperature and generally contains at least one fatty compound derived from fatty acids which have straight or branched chain, saturated or unsaturated, alkyl groups of 6–25 carbon atoms. Preferred are glyceryl esters of fatty acids. Examples of such oils include meadowfoam seed oil, apricot kernel oil, avocado oil, babassu oil, borage seed oil, castor oil, coconut oil, corn oil, hazelnut oil, olive oil, palm oil, linseed oil, and all those fatty oils disclosed on pages 507–508 of the CTFA Cosmetic Ingredient Handbook, Second Edition, 1992, which is hereby incorporated by reference. Preferred is meadowfoam seed oil.

It may also be desired to include 0.001–5%, preferably 0.005–4%, more preferably 0.005–5% by weight of one or more preservatives. The same percentage ranges of emulsifiers and humectants may also be included in the composition.

In general, the dye compositions of the invention are in the cream form, which means that they exhibit a smooth creamy texture which does not run or drip when applied to the hair.

The invention is also directed to a two component kit for oxidative dyeing of hair comprising:

A first container containing a composition comprising, by weight of the total composition:

0.0001–20% of at least one primary intermediate and at least one coupler for the formation of oxidation dyes, 0.01–10% of a 2-hydroxyphenyl benzotriazole compound which absorbs ultraviolet radiation in the wavelength range of 200 to 400 nanometers, 0.5–20% surfactant, and 10–65% water; and A second container containing a developer composition comprising, by weight of the total composition:

0.5–45% hydrogen peroxide, 0.1–10% of a silicone hair conditioning agent, 0.01–5% of an anionic polymer, and 1–99% water.

The silicone hair conditioning agents are present in the developer composition at 0.1–10%, preferably 0.5–8%, more preferably 0.5–5%, of the total developer composition. Suitable silicone hair conditioning agents include volatile or nonvolatile nonionic silicone fluids, silicone resins, and silicone semi-solids or solids.

Volatile silicones are linear or cyclic silicones having a measureable vapor pressure, which is defined as a vapor pressure of at least 2 mm. of mercury at 20° C. Examples of volatile silicones are cyclic silicones having the general formula:

$$\left[ \begin{array}{c} CH_3 \\ | \\ SiO \\ | \\ CH_3 \end{array} \right]_n$$

where n=3–7.

Also, linear volatile silicones that may be used in the compositions of the invention have the general formula:

$$(CH_3)_3Si\text{-}O\text{-}[Si(CH_3)_2\text{-}O]_n\text{-}Si(CH_3)_3$$

where n=0–7, preferably 0–5.

The silicone hair conditioning agent may comprise water insoluble nonvolatile silicone fluids including polyalkyl siloxanes, polyaryl siloxanes, polyalkylaryl siloxanes, polyether siloxane copolymers, amine-flnctional silicones, and mixtures thereof. Such silicones have the following general formula:

$$A-\underset{R}{\overset{R}{\underset{|}{Si}}}-O-\left[\underset{R}{\overset{R}{\underset{|}{Si}}}-O\right]_x\left[\underset{R'}{\overset{R}{\underset{|}{Si}}}-O\right]_y-\underset{R}{\overset{R}{\underset{|}{Si}}}-A$$

wherein R and R' are each independently alkyl, aryl, or an alkyl substituted with one or more amino groups, and x and y are each independently 0–100,000, with the proviso that x+y equals at least one and A is siloxy endcap unit. Preferred is where A is methyl, R is methyl, and R' is an alkyl substituted with at least two amino groups, most preferably an amine-functional silicone having the formula:

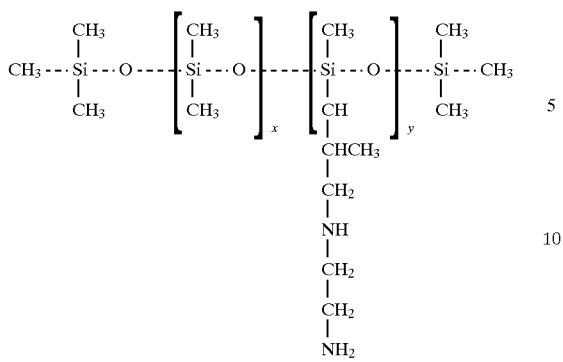

which is known by the CTFA name trimethylsilylamodimethicone.

The silicone hair conditioning agent may also be a silicone polymer having the following general formula:

wherein R, R' and R" are each independently a $C_{1-10}$ straight or branched chain alkyl or phenyl, and x and y are such that the ratio of $(RR'R")_3SiO_{1/2}$ units to $SiO_2$ units is 0.5 to 1 to 1.5 to 1.

Preferably R, R' and R" are a $C_{1-6}$ alkyl, and more preferably are methyl and x and y are such that the ratio of $(CH_3)_3SiO_{1/2}$ units to $SiO_2$ units is 0.75 to 1. Most preferred is this trimethylsiloxy silicate containing 2.4 to 2.9 weight percent hydroxyl groups which is formed by the reaction of the sodium salt of silicic acid, chlorotrimethylsilane, and isopropyl alcohol. The manufacture of trimethylsiloxy silicate is set forth in U.S. Pat. Nos. 2,676,182; 3,541,205; and 3,836,437, all of which are hereby incorporated by reference. Trimethylsiloxy silicate as described is available from Dow Corning Corporation under the tradename 2-0749 and 2-0747, each of which is a blend of about 40–60% volatile silicone and 40–60% trimethylsiloxy silicate. Dow Corning 2-0749, in particular, is a fluid containing about 50% trimethylsiloxy silicate and about 50% cyclomethicone. The fluid has a viscosity of 200–700 centipoise at 25° C., a specific gravity of 1.00 to 1.10 at 25° C., and a refractive index of 1.40–1.41.

Preferably the developer composition contains a mixture of 0.001–10%, preferably 0.005–5, more preferably 0.01–4%, of each of cyclomethicone, trimethylsiloxysilicate, and a water insoluble nonvolatile silicone, in particular trimethylsilylamodimethicone.

The developer composition also contains 0.001–5%, preferably 0.05–4%, more preferably 0.05–3%, of one or more anionic polymers such as those disclosed in U.S. Pat. No. 4,240,450, which is hereby incorporated by reference. Examples of such anionic polymers are copolymers of vinyl acetate and crotonic acid, graft copolymers of vinyl esters or acrylic or methacrylic acid esters, cross-linked graft copolymers resulting from the polymerization of at least one monomer of the ionic type, at least one monomer of the nonionic type, polyethylene glycol, and a crosslinking agent, and the like. Preferred are acrylate copolymers such as steareth-10 allyl ether acrylate copolymer.

The developer composition comprises 1–99%, preferably 10–99%, more preferably 60–97% of water.

The two containers are sold together in a kit form which is purchased by the consumer. Immediately prior to coloring the hair, the consumer mixes the contents of the containers together and applies the mixture to the hair.

Finally, the invention is directed to a method for oxidative dyeing of hair comprising the steps of:

a) applying to the hair a composition obtained by mixing Composition A and Composition B, wherein Composition A comprises, by weight of the total composition:

0.0001–20% of at least one primary intermediate and at least one coupler for the formation of oxidation dyes, 0.01–10% of a 2-hydroxyphenyl benzotiazole compound which absorbs ultraviolet radiation in the wavelength range of 200 to 400 nanometers, 0.5–20% surfactant, and 10–65% water; and Composition B comprises, by weight of the total composition:

0.5–45% hydrogen peroxide, 0.1–10% of a silicone conditioning agent, 0.01–5% of an anionic polymer, and 1–99% water, b) leaving said composition on the hair for 2 to 60 minutes, c) rinsing the hair with water.

Compositions A and B are mixed and applied to hair for an amount of time necessary to effect the desired coloration, generally 2–60, preferably 5–45, more preferably 10–35 minutes. The preferred ratio of Composition A to Composition B to achieve optimal coloration is about 0.5 to 1.5:1.0 to 2.0, preferably 1 to 1.5, respectively. After the appropriate time, the hair is rinsed with water to remove the dye mixture. The hair is allowed to dry.

The invention will be further described in connection with the following examples, which are set forth for the purpose of illustration only.

EXAMPLE 1

A composition for oxidative dyeing of hair was made as follows:

| | w/w % |
|---|---|
| Ammonium lauryl sulfate (anionic surfactant) | 2.00 |
| Propylene glycol (humectant) | 4.00 |
| Ethoxydiglycol (solvent) | 2.00 |
| Monoethanolamine (pH adjuster) | 5.00 |
| Seaweed extract (conditioner) | 0.80 |
| EDTA (chelating agent) | 0.80 |
| Isoascorbic acid (antioxidant) | 0.20 |
| Sodium sulfite (reducing agent) | 0.50 |
| Primary intermediates and couplers (dye) | 5.00 |
| Oleic acid (soap) | 12.50 |
| Cetearyl alcohol (opacifier) | 4.00 |
| Emulsifying wax (emulsifier) | 2.00 |
| Oleth-20 (nonionic surfactant) | 1.00 |
| Steareth-21 (nonionic surfactant) | 0.70 |
| Meadowfoam seed oil (oil) | 0.75 |
| Oleyl alcohol (oil) | 0.40 |
| Polyquaternium 10 (cationic conditioning agent) | 0.20 |
| Polyquaternium 28 (cationic conditioning agent) | 0.50 |
| Mica/titanium dioxide (colorant) | 0.30 |
| Hydrolyzed wheat protein (conditioner) | 1.00 |
| Cibafast W liquid* (UV absorber) | 1.00 |
| Fragrance | 0.75 |
| Ammonium hydroxide (pH adjuster) | 5.00 |
| Wheat amino acids (conditioner) | 1.00 |
| Water | QS |

*sodium isobutyl benzotriazole sulfonate, Ciba Geigy

The composition was made by first dissolving the first eight ingredients in water. The primary intermediates and couplers were then added with heat to dissolve. The remaining ingredients, except for the ammonium hydroxide, wheat amino acids, and fragrance were mixed separately and added after the primary intermediates and couplers. The remaining water, ammonium hydroxide, hydrolyzed wheat protein, wheat amino acids, and fragrance were finally added to the mixture.

EXAMPLE 2

A hydrogen peroxide-based developer for use with the hair dye composition of claim 1 was made as follows:

|  | w/w % |
| --- | --- |
| Methyl paraben reservative) | 0.05 |
| EDTA (chelating agent) | 0.02 |
| Mineral oil (oil) | 0.60 |
| Cetearyl alcohol/ceteareth-20 (80:20) (emulsifier) | 3.75 |
| Cyclomethicone/trimethylsiloxysilicate (50:50) (silicone conditioner) | 0.01 |
| Cetearyl alcohol (opacifier) | 0.40 |
| Trimethylsilylamodimethicone (silicone conditioner) | 2.00 |
| Disodium phosphate (pH adjuster) | 0.03 |
| Phosphoric acid (pH adjuster) | 0.03 |
| Hydrogen peroxide (35% solution in water) | 25.70 |
| Steareth-10 allyl ether/acrylate copolymer (anionic polymer) | 0.35 |
| Water | QS |

The preservatives were first dissolved in about half of the water. The solution was heated and the mineral oil, cetearyl alcohol/ceteareth and cetearyl alcohol were added, with stirring. The mixture was cooled and the silicones added. The disodium phosphate and phosphoric acid were dissolved in water and added to the mixture after the silicones, along with the remaining ingredients.

EXAMPLE 3

Ninety female panelists participated in an eight week double blind study designed to compare hair dyed with the compositions of Examples 1 and 2, with hair dyed using L'Oréal Preference hair color. L'Oréal Preference hair color contains the following ingredients, which are reproduced from the ingredient labeling set forth on the package:

Haircolor:
Water, cocamide DEA, butoxyethanol, PEG-2 tallow amine, SD alcohol 40, polyglyceryl-4 oleyl ether, oleyl alcohol, ammonium hydroxide, polyglyceryl-2 oleyl ether, propylene glycol, oleic acid, sodium diethylaminopropyl cocoaspartamide, pentasodium pentetate, ammonium acetate, dye Intermediates, sodium metabisulfite, fragrance, erythorbic acid, fragrance.

Color Developer:
Water, hydrogen peroxide, cetearyl alcohol, oleamide DEA, ceteareth-30, glycerin, phosphoric acid, pentasodium pentetate, sodium stannate, tetrasodium pyrophosphate.

Each panelist was tested in two four week cycles. For the first cycle, the panelist's hair was colored with the first hair color system. For a four week period, the panelist was asked to answer various questions about the color. Then that same panelist's hair was colored using the second hair color system. For a four week period, the panelists were asked to answer various questions about the color. The test results were as follows:

1. Compared to your first day of coloring, has the color of your hair lessened?

| | Percent Affirmative | | | |
| --- | --- | --- | --- | --- |
| Color | Week 1 | Week 2 | Week 3 | Week 4 |
| INVENTION | | | | |
| Champagne blond | 42 | 68 | 90 | 100 |
| Extra light ash blond | 45 | 64 | 73 | 73 |
| Light ash brown | 45 | 66 | 83 | 92 |
| Light brown | 83 | 66 | 75 | 66 |
| Medium brown | 58 | 83 | 92 | 92 |
| Dark brown | 17 | 25 | 50 | 66 |
| Light auburn | 58 | 66 | 83 | 83 |
| Average | 49 | 63 | 79 | 83 |
| L'OREAL PREFERENCE | | | | |
| Champagne blond | 56 | 78 | 83 | 83 |
| Extra light ash blond | 20 | 40 | 80 | 80 |
| Light ash brown | 66 | 83 | 83 | 83 |
| Light brown | 50 | 66 | 66 | 75 |
| Medium brown | 58 | 75 | 92 | 100 |
| Dark brown | 42 | 58 | 75 | 67 |
| Light auburn | 58 | 66 | 92 | 92 |
| Average | 50 | 68 | 82 | 83 |

2. Compared to your first day of coloring has the color of your hair remained color true?

| | Percent Affirmative | | | |
| --- | --- | --- | --- | --- |
| Color | Week 1 | Week 2 | Week 3 | Week 4 |
| INVENTION | | | | |
| Champagne blond | 74 | 63 | 53 | 42 |
| Extra light ash blond | 82 | 64 | 45 | 45 |
| Light ash brown | 83 | 58 | 50 | 42 |
| Light brown | 75 | 50 | 66 | 50 |
| Medium brown | 83 | 83 | 42 | 50 |
| Dark brown | 100 | 92 | 75 | 75 |
| Light auburn | 75 | 50 | 42 | 42 |
| Average | 81 | 66 | 53 | 49 |
| L'OREAL PREFERENCE | | | | |
| Champagne blond | 66 | 50 | 47 | 33 |
| Extra light ash blond | 90 | 80 | 66 | 60 |
| Light ash brown | 58 | 50 | 42 | 33 |
| Light brown | 83 | 66 | 83 | 50 |
| Medium brown | 66 | 58 | 42 | 42 |
| Dark brown | 92 | 92 | 67 | 67 |
| Light auburn | 92 | 66 | 16 | 8 |
| Average | 66 | 65 | 50 | 41 |

3. Do you feel the amount of color remaining in your hair is acceptable?

| PERCENT AFFIRMATIVE AFTER 4 WEEKS | | |
| --- | --- | --- |
| | INVENTION | L'OREAL PREFERENCE |
| Champagne blonde | 95 | 83 |
| Extra light ash blonde | 73 | 80 |
| Light ash brown | 92 | 67 |
| Light brown | 83 | 83 |
| Medium brown | 83 | 83 |
| Dark brown | 100 | 92 |
| Light auburn | 75 | 58 |
| Average | 87 | 78 |

4. If your haircolor has lessened, is the change (for all shades combined):

| % Barely Noticeable | | % Noticeable | | % Very Noticeable | |
|---|---|---|---|---|---|
| INV | PREF | INV | PREF | INV | PREF |
| WEEK 1 | | | | | |
| 63 | 64 | 33 | 34 | 5 | 2 |
| WEEK 2 | | | | | |
| 49 | 52 | 47 | 43 | 4 | 5 |
| WEEK 3 | | | | | |
| 47 | 47 | 50 | 40 | 3 | 18 |
| WEEK 4 | | | | | |
| 39 | 38 | 55 | 33 | 5 | 29 |

INV = invention
PREF = L'Oreal Preference

5. Mean Fading:

Mean fading was calculated for those panelists who reported fading at intervals of one, two, three, and four weeks, with seven shades pooled. The panelists who reported fading after intervals of one, two, three, and four weeks were asked to rate the fading on a scale of 1 to 3 with 1 being the best and 3 being the worst. The numerical results obained were averaged to arrive at the mean.

| Hair Color | Mean | Standard Error |
|---|---|---|
| Invention (n = 74) | 1.66A | 0.07 |
| L'Oreal Preference (n = 72) | 1.92 | 0.10 |

The above results illustrate that the hair dye composition of the invention exhibited improved colorfastness after three weeks, as compared to L'Oréal Preference haircolor.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A composition for oxidative dyeing of hair comprising, by weight of the total composition:

0.0001–20% of at least one primary intermediate and at least one coupler for the formation of oxidation dyes, 0.01–10% of a 2-hydroxyphenyl benzotriazole compound having the formula:

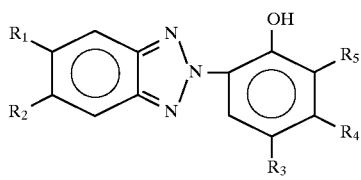 (a)

wherein $R_1$, $R_2$, $R_3$, $R_4$, and $R_5$ are each independently H, hydroxyl, carboxyl, halogen, or $C_{1-40}$ straight or branched chain alkyl, $C_{1-40}$ straight or branched chain alkoxy, $C_{2-20}$ alkoxycarbonyl, carboxy, $C_{1-40}$ alkyl substituted phenyl, $C_{5-6}$ cycloalkyl, $SO_3H$, $SO_3Na'$, or

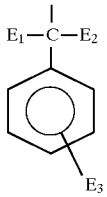

wherein $E_1$ and $E_2$ are each independently H, or $C_{1-4}$ alkyl, and $E_3$ is H, halogen, or $C_{1-4}$ alkyl, 0.5–20% surfactant, and 10–65% water.

2. The composition of claim 1 whrein $R_1$ and $R_2$ are H.

3. The composition of claim 2 wherein $R_3$ is $SO_3Na$ or $SO_3H$.

4. The composition of claim 3 wherein $R_5$ is a $C_{1-10}$ straight or branched chain alkyl.

5. The composition of claim 3 wherein $R_1$, $R_2$, and $R_4$ are H, $R_3$ is $SO_3Na$, and $R_5$ is a $C_{1-10}$ branched chain alkyl.

6. The composition of claim 1 wherein the 2-hydroxyphenyl benzotriazole is sodium isobutyl benzotriazole sulfonate.

7. The composition of claim 1 additionally comprising a cationic hair conditioning agent selected from the group consisting of:

(a) quaternary ammonium salts have the formula:

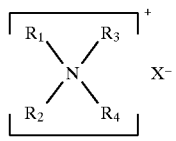

wherein $R_1$ is hydrogen, an aliphatic group of 1 to 22 carbon atoms, or aromatic, aryl, or alkaryl group having 12 to 22 carbon atoms; $R_2$ is an aliphatic group having 1–22 carbon atoms; $R_3$ and $R_4$ are each alkyl groups of from 1 to 3 carbon atoms, and X is an anion selected from halogen, acetate, phosphate, nitrate and methyl sulfate radicals; and (b) (i) cationic derivatives of cellulose ethers, (ii) copolymers of vinyl pyrrolidone, (iii) homopolymers of dimethyldiallylammonium chloride, (iv) copolymers of dimethyldiallylammonium chloride and acrylamide, (v) homopolymers or copolymers of acrylic or methacrylic acid, and (vi) and mixtures thereof.

8. The composition of claim 7 wherein the cationic hair conditioning agent is a copolymer of vinylpyrrolidone having monomer units of the formula:

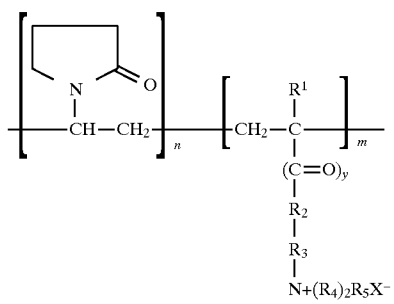

wherein $R^1$ is hydrogen or methyl, y is 0 or 1, $R^2$ is O or NH, $R^3$ is $C_xH_{2x}$ where x is 2 to 18, or —$CH_2$—CHOH—$CH_2$—, R is methyl, ethyl, phenyl, or $C_{1-4}$ substituted phenyl, and $R^5$ is methyl or ethyl.

9. The composition of claim 8 wherein $R^1$ is methyl.

10. The composition of claim 9 wherein $R_2$ is NH.

11. The composition of claim 10 herein $R_3$ is $CH_2CH_2$, $R_4$ is methyl, and $R_5$ is methyl.

12. The composition of claim 1 wherein the surfactant is selected from the group consisting of an anionic surfactant, a nonionic surfactant, an amphoteric surfactant, a zwitterionic surfactant, and mixtures thereof.

13. The composition of claim 12 wherein the surfactant is selected from the group consisting of an anionic surfactant, a nonionic surfactant, and mixtures thereof.

14. The composition of claim 13 wherein the anionic surfactant is an alkyl sulfate having the formula $ROSO_3M$, an alkyl ether sulfate having the formula $RO(C_2H_4O)_xSO_3M$ wherein R is alkyl or alkenyl of from about 10 to 20 carbon atoms, x is 1 to 10 and M is a water soluble cation such as ammonium, sodium potassium, or triethanolamine.

15. The composition of claim 13 wherein the nonionic surfactant is the condensation product of ethylene oxide and an aliphatic alcohol having 8 to 18 carbon atoms.

16. The composition of claim 1 further comprising 0.01–10% of a fatty oil.

17. The composition of claim 16 wherein the fatty oil is meadowfoam seed oil.

* * * * *